United States Patent [19]

Hattori

[11] 4,356,534
[45] Oct. 26, 1982

[54] LIGHT SUPPLY DEVICE FOR AN ENDOSCOPE

[75] Inventor: Shinichiro Hattori, Tokyo, Japan

[73] Assignee: Olympus Optical Co., Ltd., Tokyo, Japan

[21] Appl. No.: 195,440

[22] Filed: Oct. 9, 1980

[30] Foreign Application Priority Data

Oct. 19, 1979 [JP] Japan .............................. 54/134145
Oct. 19, 1979 [JP] Japan .............................. 54/134146

[51] Int. Cl.³ .............................................. F21V 7/04
[52] U.S. Cl. ....................................... 362/32; 362/95;
362/276; 362/285; 362/295; 362/802; 362/804
[58] Field of Search .................... 362/26, 27, 32, 95,
362/265, 277, 286, 293, 295, 321, 394, 802, 804,
212, 276, 287, 285; 128/6

[56] References Cited

U.S. PATENT DOCUMENTS

| | | | |
|---|---|---|---|
| 1,434,404 | 11/1922 | Nordstedt | 362/286 |
| 1,678,093 | 7/1928 | Wood | 362/212 |
| 3,382,353 | 10/1980 | Wappler | |
| 3,599,922 | 8/1971 | Junginger | 362/276 X |
| 3,670,722 | 6/1972 | Kosaka | 128/6 |
| 3,683,167 | 10/1980 | Rishton | |
| 3,831,017 | 10/1980 | Auer | |
| 4,009,382 | 2/1977 | Nath | 362/32 |
| 4,023,034 | 5/1974 | Schacht | 362/276 X |
| 4,025,776 | 10/1980 | Cawood et al. | |
| 4,179,175 | 12/1979 | Farnworth et al. | 200/51.09 |
| 4,234,819 | 11/1980 | Maxey | 362/276 X |
| 4,285,033 | 8/1981 | Hart | 362/295 |

FOREIGN PATENT DOCUMENTS

2417058 9/1979 France .................. 362/277

Primary Examiner—Peter A. Nelson
Attorney, Agent, or Firm—Frishauf, Holtz, Goodman & Woodward

[57] ABSTRACT

A connector is connected to an endoscope through a universal cord into which a light guide is inserted. A socket is fixed to a housing to receive the connector. A light is emitted from a lamp and, after being reflected by a reflective mirror, is transmitted into a distal end of the light guide which extends from the socket. The lamp is connected through a dimmer circuit to a power source and a relay switch is provided between the lamp and the dimmer circuit. The relay switch is opened and closed by a solenoid which is connected to a power source through a detector which detects whether the connector is received in the socket.

9 Claims, 3 Drawing Figures

LIGHT SUPPLY DEVICE FOR AN ENDOSCOPE

BACKGROUND OF THE INVENTION

This invention relates to a light supply device for an endoscope which emits a light toward an endoscope.

According to a conventional endoscope system, a connector of a universal cord of an endoscope is detachably inserted into the socket of a light supply device. A light of observation is incident from the lamp of the light supply device onto the end surface of the light guide of the endoscope which extends through the socket. The light incident on the end surface of the light guide is transmitted through the light guide to the distal end of the endoscope to permit a region of interest of a subject to be illuminated thereby.

In such conventional light supply device, if the connector of the universal cord is removed from the socket of the light supply device during the lighting of the lamp, the light of the lamp leaks to the outside through the socket. When such light reaches the user's eyes (for example, the doctor's eyes or the patient's eyes), the user's eyes are dazzled by the light and there is a possibility that a bad effect will be imparted to his eyes.

It is accordingly an object of this invention to provide a light supply device for an endoscope which prevents the user's eyes from being dazzled by light leaking through the socket of the light supply device.

SUMMARY OF THE INVENTION

According to the light supply device of this invention, a connector of a universal cord of the endoscope is detachably inserted into the socket of a light supply device. The light supply device includes a lamp for emitting a predetermined amount of light into a light guide of the endoscope. A light control means is provided for decreasing an amount of light which leaks through the socket of the light supply device when the connector is removed from the socket of the light supply device.

DETAILED DESCRIPTION

Figure 1:
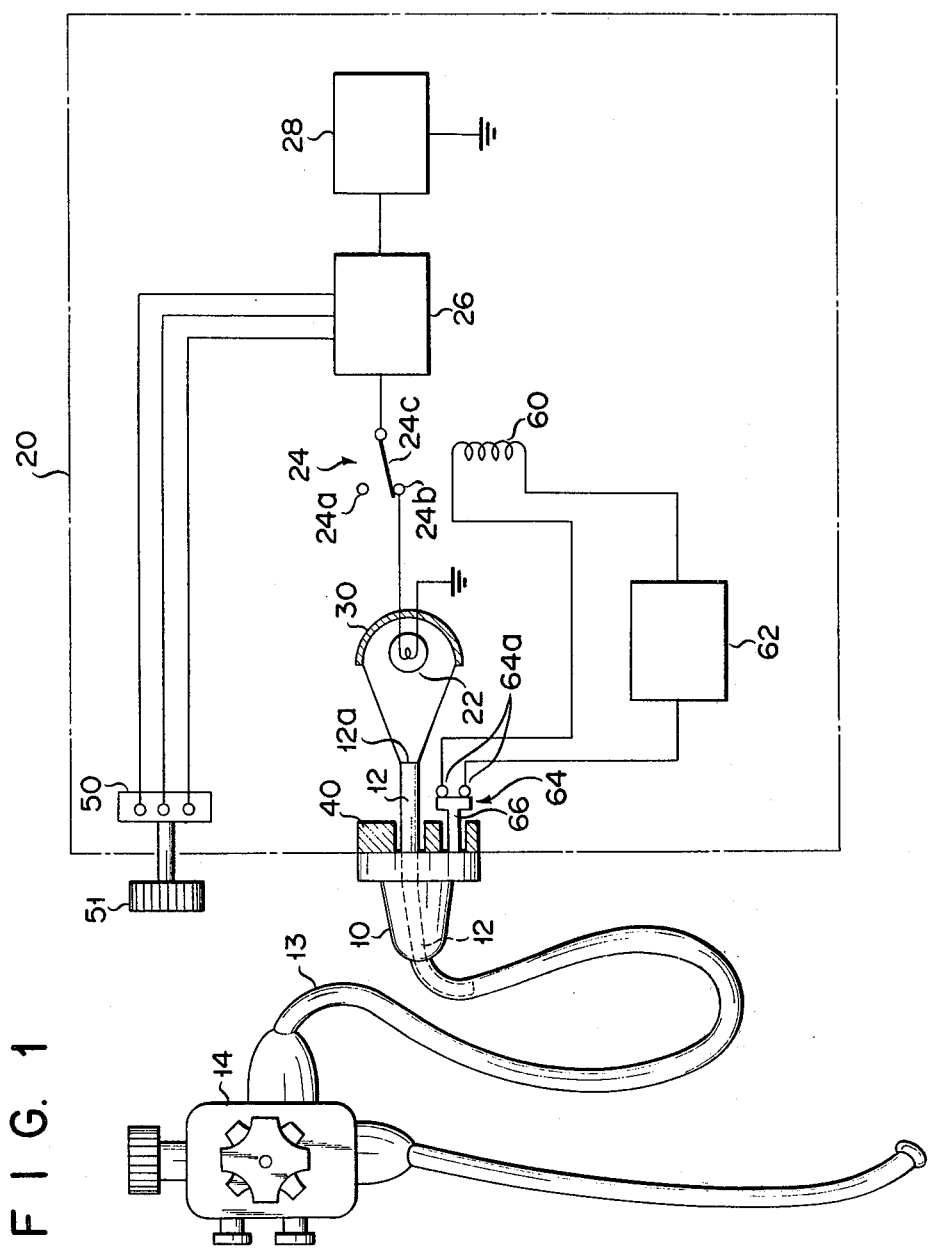
FIG. 1 is a block diagram showing a light supply device for an endoscope according to one embodiment of this invention.

In FIG. 1, an universal cord 13 in which a light guide 12 for transmitting a light of observation is received is provided at one end with a connector 10. The other end of the universal cord 13 is connected to an operation section of an endoscope 14. The light guide 12 is formed by bundling together a predetermined number of optical fibers. A light source device 20 includes a light source, for example, a lamp 22 such as a halogen lamp, Xenon lamp or arc lamp. The lamp 22 is connected to a power source 28 through a relay switch 24 and dimmer circuit 26. A reflective mirror 30 is provided behind the lamp 22. Mirror 30 is bowl-shaped such that it has, for example, an elliptical outer configuration. The focal point of the reflective mirror 30 is set such that it is located opposite to the distal end 12a of the light guide 12 which extends through the socket 40 into the light supply device 20. In consequence, light emitted from the lamp 22 is reflected on the inner surface of the reflective mirror 30, condensed toward the distal end 12a of the light guide 12 and transmitted to the proximal end of the endoscope 14 through the light guide 12. The dinner circuit 26 is comprised of, for example, a phase-control dimmer circuit using a conventionally known thyristor. An amount of light emitted from the lamp 22 can be continuously controlled by operating a knob 51 of a variable resistor (volume) 50 which is connected to the dimmer circuit 26. The variable resistor 50, together with the socket 40, is fixed to the housing of the light supply device 20.

The relay switch 24 includes a normal closed contact 24a, a normal open contact 24b connected to the lamp 22 and a movable contact 24c connected to the dimmer circuit 26. The relay switch 24 is operated by a solenoid 60. That is, the movable contact 24c is connected to the contact 24b when the solenoid 60 is energized and connected to the contact 24a when the solenoid 60 is deenergized. The solenoid 60 is connected to a power source 62 through a detector 64. The detector 64 comprises contacts 64a and a movable contact 66 which extends from an abutting surface between the socket 40 and the connector 10. The contacts of the detector 64 are closed by the movable contact 66 when the connector 10 is inserted into the socket 40 and opened when the connector 10 is removed from the socket 40.

While the connector 10 is inserted into the socket 40, the movable contact 66 of the detector 64 is projected toward the inside of the housing 20 to cause the contacts of the detector 64 to be closed. At this time, an electric current from the power source 62 flows through the solenoid 60 to cause the solenoid to be energized. As a result, the movable contact 24c of the relay switch 24 is connected to the contact 24b, causing the electric current from the power source 28 to be supplied to the lamp 22 through the dimmer circuit 26 to permit the lamp 22 to be lit. While, on the other hand, the connector 10 is detached from the socket 40, the contacts of the detector 64 are opened. Since the solenoid 60 is deenergized, the movable contact 24c of the relay switch 24 is returned to the side of the contact 24a. As a result, the electric current flowing from the power source 28 through the dimmer circuit 26 to the lamp 22 is interrupted by the relay switch 24, extinguishing the lamp 22. For this reason, the light emission through the socket 40 to the outside of the light supply device 20 is prevented, thereby preventing the user's eyes (for example, doctor's eyes of patient's eyes) from being exposed to leaking light.

Figure 2:
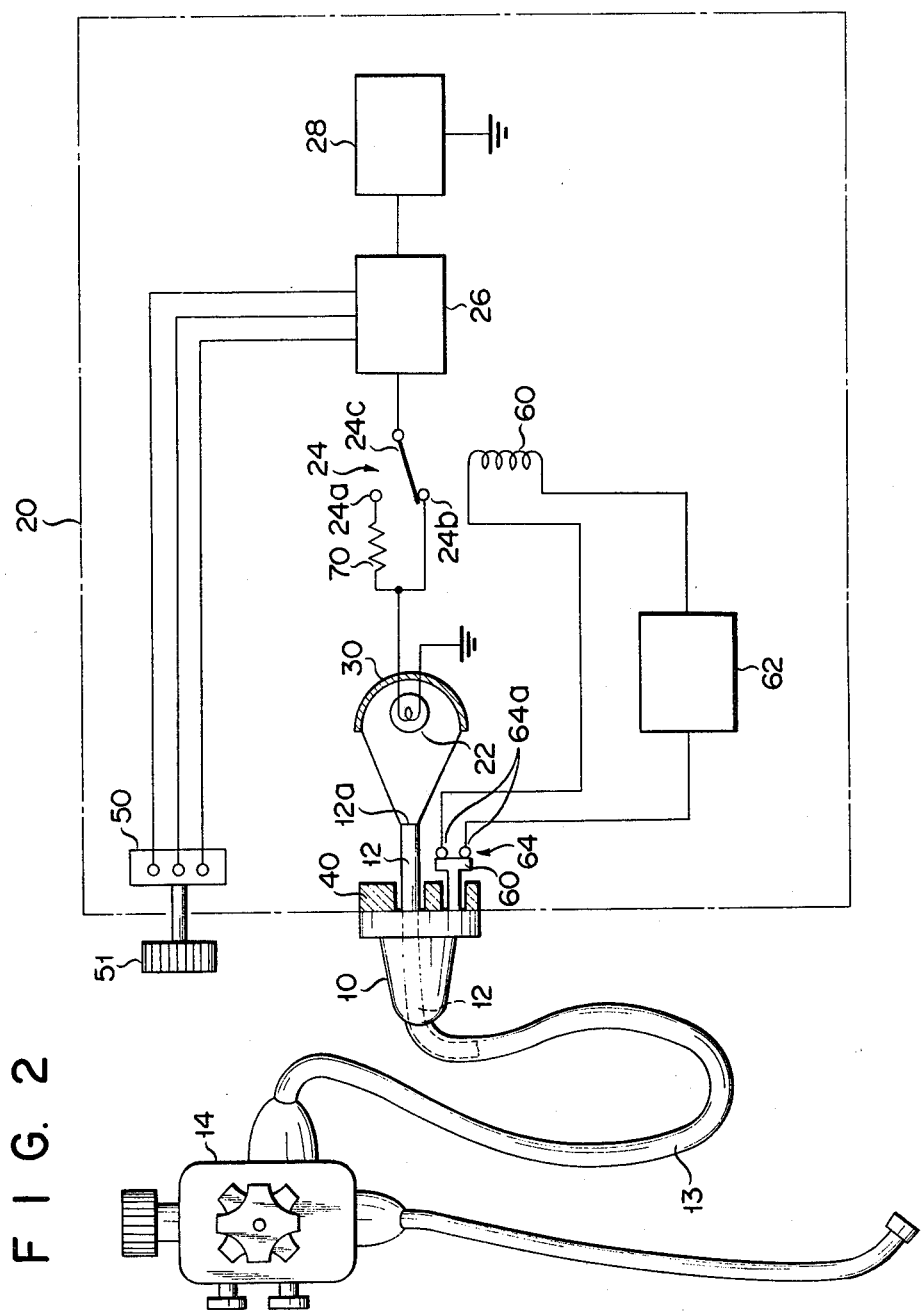
FIG. 2 is a block diagram showing a light supply device for an endoscope according to another embodiment of this invention.

In an embodiment shown in FIG. 2, a normally closed contact 24a of a relay switch 24 is connected to the lamp 22 through a resistor 70 of a predetermined value (for example, five times the resistance of the lamp 22). A normally open contact 24b of the relay switch 24 is connected directly to the lamp 22. The remaining arrangement of this embodiment is the same as that of the first embodiment and further explanation thereof is omitted for brevity.

According to the embodiment of FIG. 2, when a connector 10 is detached from the socket 40, the contacts 64a of a detector 64 are closed by a movable contact 66, causing an electric current from a power source 62 to flow through and energize a solenoid 60. As a result, a movable contact 24c is switched from the contact 24b to the contact 24a. As a result, an electric current from a power source 28 flows into the lamp 22 through the resistor 70 which is connected to the contact 24a of the relay switch 24, thus decreasing an amount of light emitted from the lamp 22. Since an amount of light leaking through a socket 40 is decreased, the user's eyes are prevented from being dazzled and thus the user's eyes are protected against an otherwise intense light.

According to this embodiment, as a smaller amount of light is emitted through the socket 40 during a time period in which the connector 10 is removed from the socket 40, if the filament of the lamp 22 is burned out, the user can readily discover the faulty lamp 22 before the endoscope is used.

Although in the above-mentioned embodiments the light from the light supply device is interrupted or attenuated by controlling a power supply to the light source, it is possible to shield or attenuate the light from the light supply device by using a shield plate or a filter. That is, according to an embodiment shown in FIG. 3, a lamp 22 in a light supply device 20 is connected to a power source 28 through a dimmer circuit 26. Behind the lamp 22 is disposed a reflective mirror 30 which is the same as that of the preceding embodiments. A solenoid 60 is connected to the power source 62 and a detector 80 is connected in series between the solenoid 60 and the power source 62. The detector 80 comprises a pair of projection pins 81a, 81b mounted on a connector 10 and a pair of pin sockets 82a, 82b which are provided on the socket 40 and into which the projection pins are inserted. A shutter plate 84 is mounted on a movable rod 60a of the solenoid 60 and, when the solenoid 60 is demagnetized, the shutter plate 84 is inserted by a spring 86 between the lamp 22 and a distal end 12a of a light guide 12. The remaining arrangement of the FIG. 3 embodiment is the same as that of the preceding embodiment and further explanation is therefore omitted.

According to this embodiment, when the connector 10 is removed from the socket 40, the pins 81a and 81b of the detector 80 are respectively disconnected from the sockets 82a and 82b, causing the detector 80 to be opened to permit the solenoid 60 to be demagnetized. Since at this time the shutter plate 84 is inserted under the urging force of the spring 86 between the lamp 22 and the distal end 12a of the light guide 12, all the light reflected on the reflective mirror 30 is shielded by the shutter plate 84. As a result, no light leaks through the socket 40 and thus the user's eyes are prevented from being dazzled by the light. Where the shutter plate 84 is formed of a light attenuating filter, an amount of light from the lamp 22 is attenuated by the light attenuating filter so that the user's eyes are not dazzled by the light leaking through the socket 40. Where the light attenuating filter is used, if the filament of the lamp 22 is burned out, the user can discover a faulty lamp 22 before the endoscope is used.

Although this invention has been shown and described in connection with particular embodiments, variations, changes and modifications may be made within the spirit and scope of the invention. For example, the solenoid may be excited during the time period in which the connector is removed from the socket so that the movable contact of the relay switch can be moved into contact with the normally open contact. Alternatively, the shutter plate may be projected between the lamp and the distal end of the light guide so as to decrease an amount of light leaking through the socket of the light supply device. Even if in this case a mechanism such as a solenoid is faulty, a light transmission to an endoscope now in use is maintained, permitting examination under the endoscope and improving the reliability of the light source for the endoscope. A liquid crystal or a mechanical shutter mechanism may be used in place of the shutter plate of FIG. 3. A motor may be used in place of the solenoid to drive a relay switch and shutter plate. In this case, the motor is connected to an electronic detection circuit adapted to be operated during the time period in which the connector is removed from the socket. In summary, it is only necessary that a mechanism be provided for attenuating an amount of light emitted through the socket of the light supply device during the time period in which the connector of the endoscope is removed from the socket.

I claim:

1. A light supply device which includes a housing and which supplies illumination light to an endoscope having a connector connected to light guide means which transmits the illumination light to the endoscope, comprising:
   light source means mounted within said housing for emitting light when energized;
   power source means mounted within said housing and connected to said light source means for supplying electric power to said light source means to energize said light source means;
   a socket mounted on said housing and to which said connector of said endoscope is detachably connected, said socket having an opening through which said light guide means extends when said connector is connected to said socket;
   light converging means for converging said light emitted from said light source means and for causing said light from said light source means to be incident onto said light guide means when said connector of said endoscope is connected to said socket; and
   light control means coupled to said light source means and including detection means for detecting the state of the connection between said connector of said endoscope and said socket; and means for causing an amount of light from said light source means to be decreased to a predetermined level when said detection means detects that said connector is disconnected from said socket.

2. The light supply device of claim 1, wherein said detection means of said light control means comprises means mounted in said socket for detecting the disconnection of said connector from said socket and for generating a predetermined detection signal responsive to detecting such disconnection; and light amount alleviating means connected to said detecting means and responsive to said detection signal from said detecting means for causing a decrease in an amount of light which is emitted from said light source means and transmitted to said opening of said socket, thereby at least decreasing the amount of light which leaks toward the outside of the housing through said opening in said socket when said connector is disconnected from said socket.

3. The light supply of claim 2, wherein said detecting means which detects disconnection of said connector from said socket includes switching means operated in ON-OFF fashion according to the connection or disconnection of said connector to or from said socket.

4. The light supply device of claim 3, wherein said light amount alleviating means includes electric power control means coupled between said power source means and said light source means for causing electric power which is supplied from said power source means to said light source means in response to the ON and OFF operation of said switching means to be lowered to a predetermined level, thereby decreasing the amount of light directly emitted from said light source means.

5. The light supply device of claim 4, wherein said electric power control means includes variable resistor means coupled between said power source means and said light source means, the resistance value of said variable resistor means being variable at least between a first resistive value and a second resistive value; and drive means coupled between said switching means and said variable resistor means for driving said variable resistor means between at least said first and second resistive values in response to the ON and OFF operation of said switching means, such that when said connector of the endoscope is disconnected from said socket, the resistance value of said variable resistor means is varied by said drive means from said first resistive value to said second resistive value to restrict the electric current from said power source means to said light source means to a lower than normal value to decrease the amount of light emitted from said light source means.

6. The light supply device of claim 3, wherein said light amount alleviating means includes electric power control means coupled between said power source means and said light source means, and being responsive to said detecting means for causing the electric power which is supplied from said power source means to said light source means to be lowered to a predetermined level responsive to said predetermined detection signal from said detecting means, thereby decreasing the amount of light directly emitted from said light source means.

7. The light supply device of claim 3, wherein said light amount alleviating means includes filter means disposed between said light source means and said socket, said filter means being movable in response to the ON-OFF operation of said switching means to extend, upon detection that said connector is disconnected from said socket, into the path of the light which is emitted from the light source means and converged by said light-converging means to said opening of said socket, to cause the light transmitted from said light source into said opening of said socket to be decreased to a predetermined level.

8. The light supply device of claim 3, wherein said light amount alleviating means includes filter means disposed between said light source means and said socket, said filter means being movable in response to said predetermined detection signal from said detecting means which indicates that said connector is disconnected from said socket, into the path of the light which is emitted from the light source means and converged by said light converging means to said opening of said socket, to cause the light transmitted from said light source into said opening of said socket to be decreased to a predetermined level.

9. The light supply device of claim 1, wherein said light-converging means includes a reflective mirror member disposed near said light source means and having a substantially bowl-like shape, said reflective mirror member converging the light from said light source means, upon connecting of said connector to said endoscope to said socket, toward said light guide means which extends through said opening of said socket when said connector of the endoscope is connected to said socket.

* * * * *

UNITED STATES PATENT AND TRADEMARK OFFICE
CERTIFICATE OF CORRECTION

PATENT NO. : 4,356,534

DATED : October 26, 1982

INVENTOR(S) : Shinichiro Hattori

Page 1 of 5

It is certified that error appears in the above-identified patent and that said Letters Patent is hereby corrected as shown below:

The title page should be deleted to appear as per attached title page.

Figure 3:
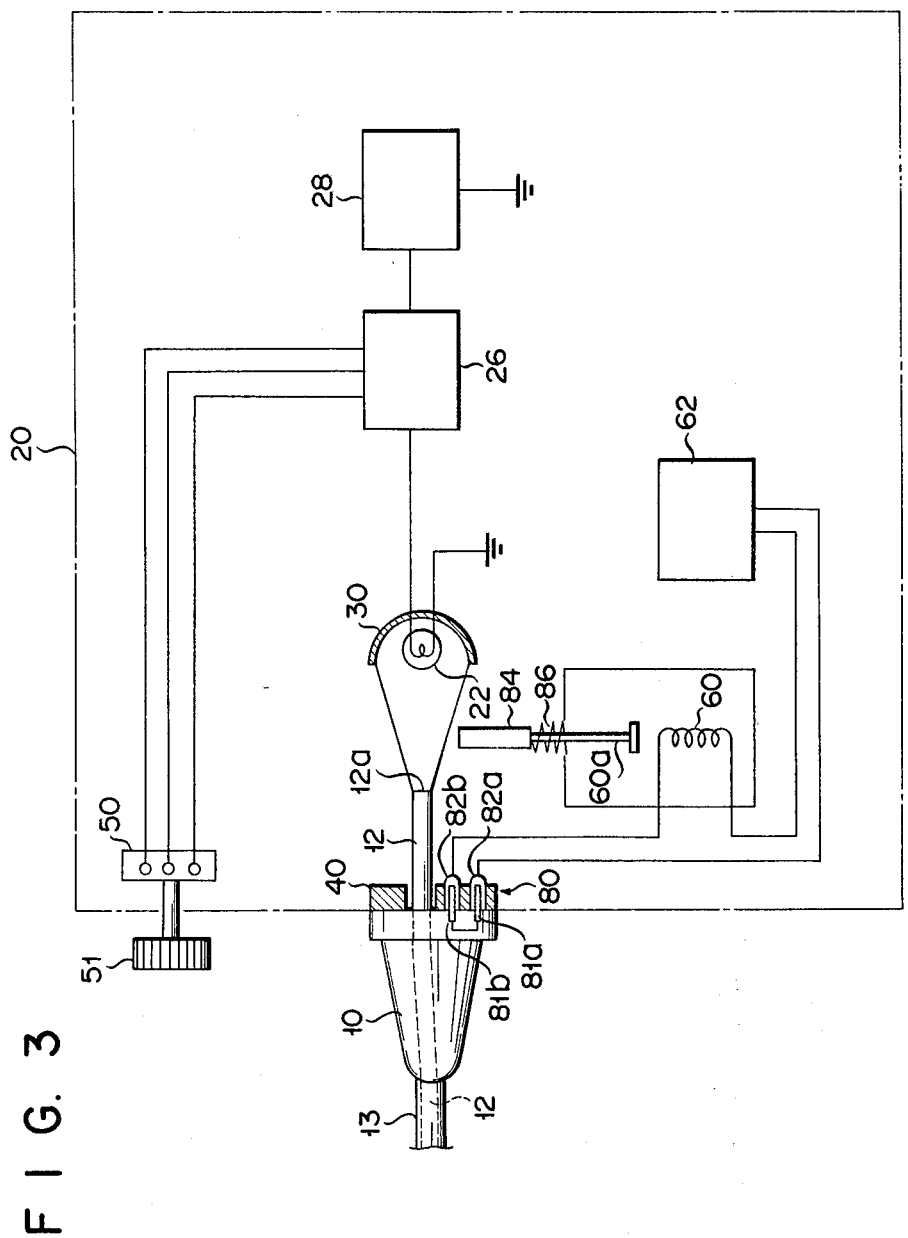
FIG. 3 is a block diagram showing a light supply device for an endoscope according to another embodiment of this invention.
Figure 1:
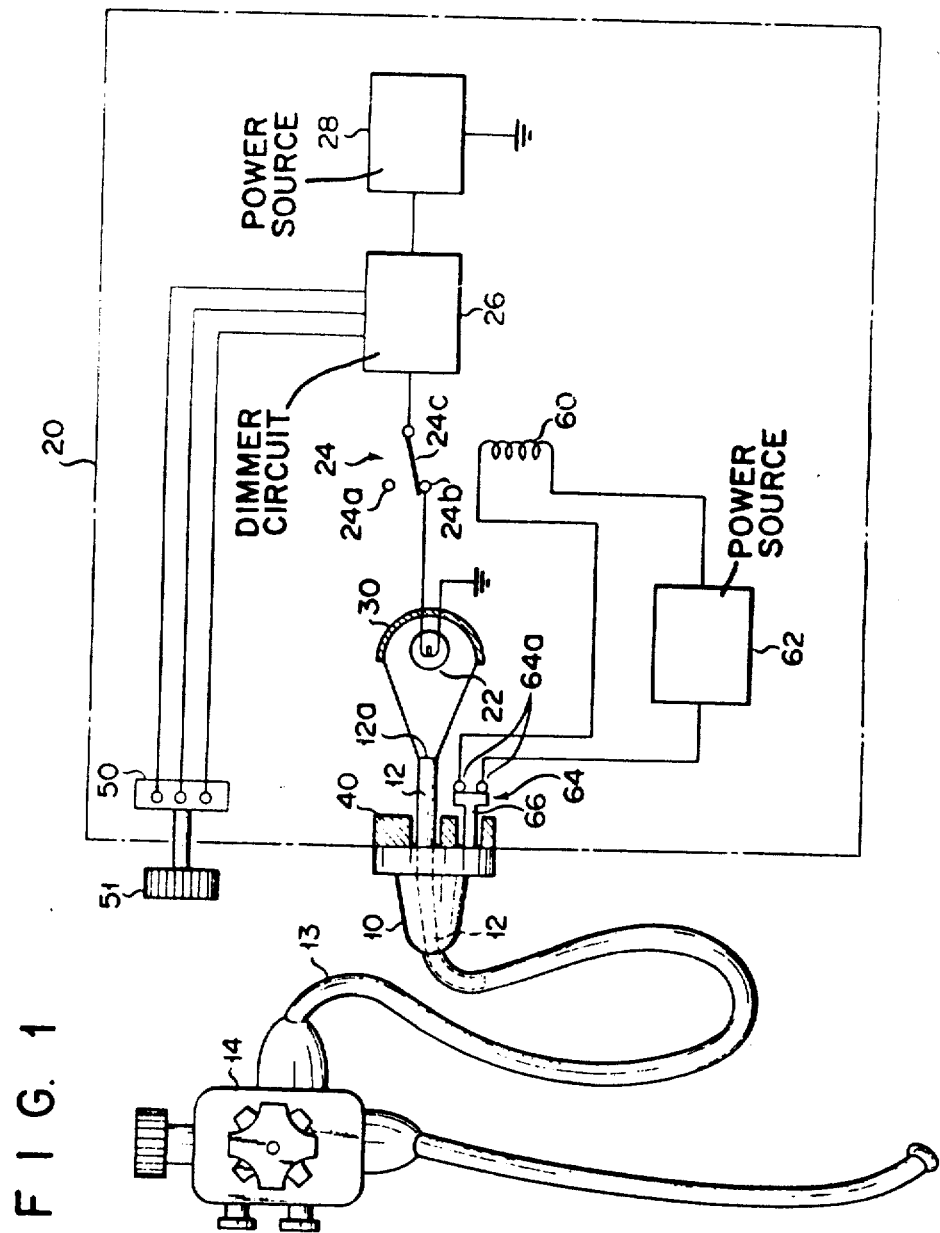
Figure 2:
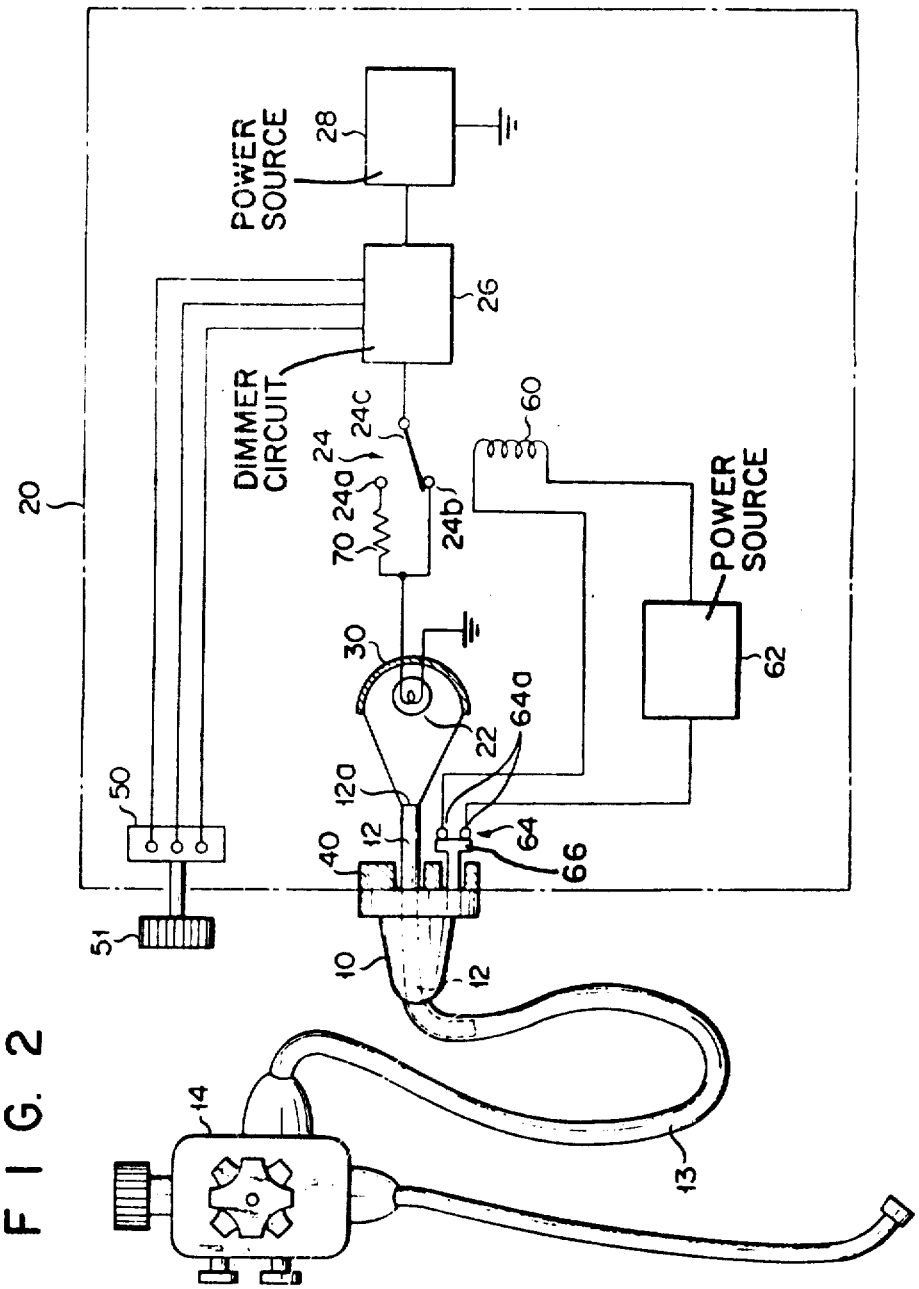
Figure 3:
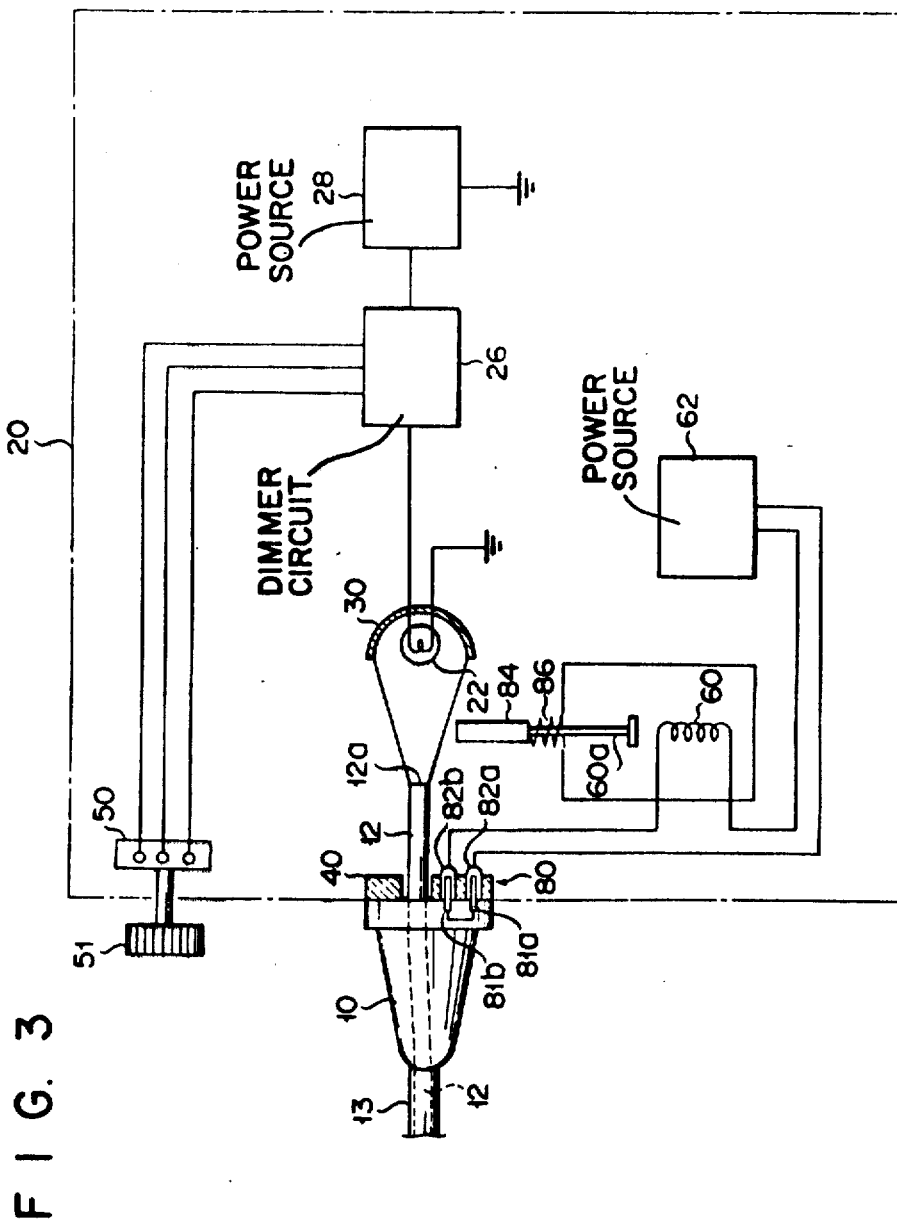

Figures 1, 2 and 3 should appear as shown on the the attached sheets.

Signed and Sealed this

Twenty-sixth Day of April 1983

[SEAL]

Attest:

Attesting Officer

GERALD J. MOSSINGHOFF

Commissioner of Patents and Trademarks

United States Patent [19]

Hattori

[11] 4,356,534
[45] Oct. 26, 1982

[54] LIGHT SUPPLY DEVICE FOR AN ENDOSCOPE

[75] Inventor: Shinichiro Hattori, Tokyo, Japan

[73] Assignee: Olympus Optical Co., Ltd., Tokyo, Japan

[21] Appl. No.: 195,440

[22] Filed: Oct. 9, 1980

[30] Foreign Application Priority Data

Oct. 19, 1979 [JP] Japan ............... 54/134145
Oct. 19, 1979 [JP] Japan ............... 54/134146

[51] Int. Cl.³ ............................................. F21V 7/04
[52] U.S. Cl. .............................. 362/32; 362/95;
362/276; 362/285; 362/295; 362/802; 362/804
[58] Field of Search ............... 362/26, 27, 32, 95,
362/265, 277, 286, 293, 295, 321, 394, 802, 804,
212, 276, 287, 285; 128/6

[56] References Cited

U.S. PATENT DOCUMENTS

| 1,434,404 | 11/1922 | Nordstedt | 362/286 |
|---|---|---|---|
| 1,678,093 | 7/1928 | Wood | 362/212 |
| 3,382,353 | 10/1980 | Wappler | . |
| 3,599,922 | 8/1971 | Junginger | 362/276 X |
| 3,670,722 | 6/1972 | Kosaka | 128/6 |
| 3,683,167 | 10/1980 | Rishton | . |
| 3,831,017 | 10/1980 | Auer | . |
| 4,009,382 | 2/1977 | Nath | 362/32 |
| 4,023,034 | 5/1974 | Schacht | 362/276 X |
| 4,025,776 | 10/1980 | Cawood et al. | . |
| 4,179,175 | 12/1979 | Farnworth et al. | 200/51.09 |
| 4,234,819 | 11/1980 | Maxey | 362/276 X |
| 4,285,033 | 8/1981 | Hart | 362/295 |

FOREIGN PATENT DOCUMENTS 2417058 9/1979 France ............... 362/277

*Primary Examiner*—Peter A. Nelson
*Attorney, Agent, or Firm*—Frishauf, Holtz, Goodman & Woodward

[57] ABSTRACT

A connector is connected to an endoscope through a universal cord into which a light guide is inserted. A socket is fixed to a housing to receive the connector. A light is emitted from a lamp and, after being reflected by a reflective mirror, is transmitted into a distal end of the light guide which extends from the socket. The lamp is connected through a dimmer circuit to a power source and a relay switch is provided between the lamp and the dimmer circuit. The relay switch is opened and closed by a solenoid which is connected to a power source through a detector which detects whether the connector is received in the socket.

9 Claims, 3 Drawing Figures

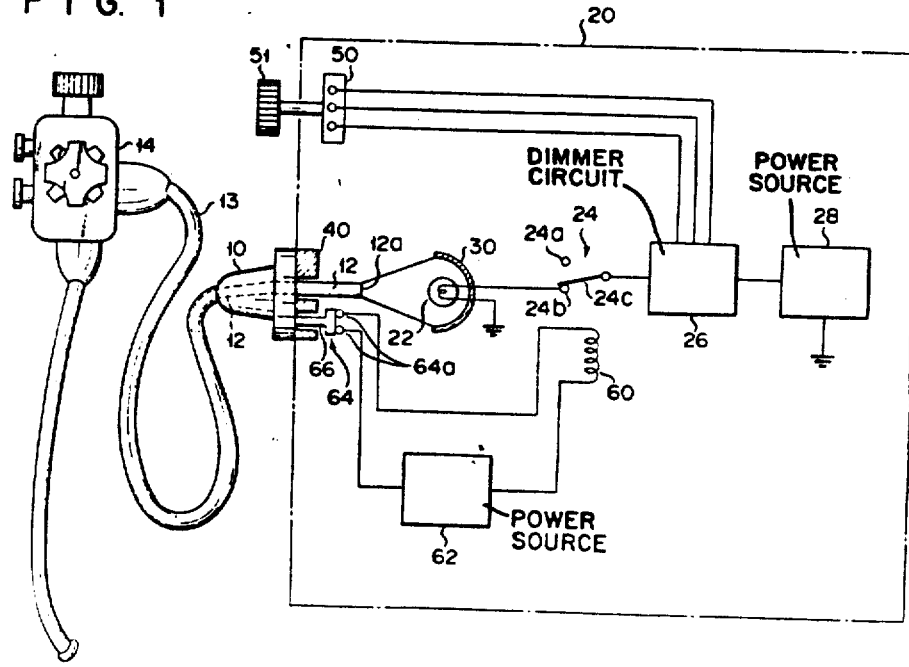

FIG. 1